US008859805B2

(12) United States Patent
Mattke et al.

(10) Patent No.: US 8,859,805 B2
(45) Date of Patent: Oct. 14, 2014

(54) PROCESS FOR PREPARING ISOCYANATES

(75) Inventors: Torsten Mattke, Freinsheim (DE);
Matthias Kloetzer, Kroppen (DE);
Eckhard Stroefer, Mannheim (DE);
Bernhard Geissler, Kirchheim (DE);
Peter Zehner, Weisenheim am Berg (DE)

(73) Assignee: BASF SE, Ludwigshafen (DE)

( * ) Notice: Subject to any disclaimer, the term of this patent is extended or adjusted under 35 U.S.C. 154(b) by 97 days.

(21) Appl. No.: 13/394,647

(22) PCT Filed: Sep. 9, 2010

(86) PCT No.: PCT/EP2010/063225
§ 371 (c)(1),
(2), (4) Date: Mar. 7, 2012

(87) PCT Pub. No.: WO2011/036062
PCT Pub. Date: Mar. 31, 2011

(65) Prior Publication Data
US 2012/0172621 A1    Jul. 5, 2012

(30) Foreign Application Priority Data
Sep. 22, 2009 (EP) .................... 09170992

(51) Int. Cl.
*C07C 263/00* (2006.01)
*C07C 261/00* (2006.01)
(52) U.S. Cl.
USPC .......................... 560/345; 560/132
(58) Field of Classification Search
USPC ................................. 560/345, 132
See application file for complete search history.

(56) References Cited

U.S. PATENT DOCUMENTS

| 5,744,633 | A | 4/1998 | Wilmes et al. | |
| 8,193,385 | B2 * | 6/2012 | Kloetzer et al. | 560/344 |
| 2005/0250960 | A1 | 11/2005 | Kohlstruk et al. | |
| 2008/0249332 | A1 * | 10/2008 | Klotzer et al. | 560/344 |
| 2011/0137067 | A1 | 6/2011 | Franzke et al. | |
| 2011/0178329 | A1 | 7/2011 | Bock et al. | |
| 2011/0207961 | A1 | 8/2011 | Geissler et al. | |
| 2011/0251425 | A1 | 10/2011 | Penzel et al. | |
| 2011/0313192 | A1 | 12/2011 | Rosendahl et al. | |

FOREIGN PATENT DOCUMENTS

| EP | 0 018 588 | 11/1980 |
| EP | 0 027 952 | 5/1981 |
| EP | 0 028 338 | 5/1981 |
| EP | 0 126 299 | 11/1984 |

(Continued)

OTHER PUBLICATIONS

U.S. Appl. No. 13/434,135, filed Mar. 29, 2012, Lehr, et al.

(Continued)

*Primary Examiner* — Karl J Puttlitz
(74) *Attorney, Agent, or Firm* — Oblon, Spivak, McClelland, Maier & Neustadt, L.L.P.

(57) ABSTRACT

The invention relates to a multistage process for the continuous preparation of organic, distillable polyisocyanates, preferably diisocyanates, particularly preferably aliphatic or cycloaliphatic diisocyanates, by reaction of the corresponding organic polyamines with carbonic acid derivatives and alcohols to form low molecular weight monomeric polyurethanes and thermal dissociation of the latter, in which the polyisocyanates produced and unusable residues are separated off at particular stages of the reaction and reusable by-products and intermediates are recirculated to preceding stages.

17 Claims, 2 Drawing Sheets

(56) References Cited

FOREIGN PATENT DOCUMENTS

| | | |
|---|---|---|
| EP | 0 566 925 | 10/1993 |
| EP | 0 657 420 | 6/1995 |
| EP | 1 593 669 | 11/2005 |
| WO | 2007 031444 | 3/2007 |
| WO | 2007 036479 | 4/2007 |

OTHER PUBLICATIONS

U.S. Appl. No. 13/513,460, filed Jun. 1, 2012, Bock, et al.
U.S. Appl. No. 13/587,378, filed Aug. 16, 2012, Mattke, et al.
International Search Report Issued Apr. 5, 2011 in PCT/EP10/63225 Filed Sep. 9, 2010.
U.S. Appl. No. 13/479,961, filed May 24, 2012, Stroefer, et al.

* cited by examiner

PROCESS FOR PREPARING ISOCYANATES

The invention relates to a multistage process for the continuous preparation of organic, distillable polyisocyanates, preferably diisocyanates, particularly preferably aliphatic or cycloaliphatic diisocyanates, by reaction of the corresponding organic polyamines with carbonic acid derivatives and alcohols to form low molecular weight monomeric polyurethanes and thermal dissociation of the latter, in which the polyisocyanates produced and unusable residues are separated off at particular stages of the reaction and reusable by-products and intermediates are recirculated to preceding stages.

Industrial processes for preparing organic polyisocyanates, e.g. aromatic, aliphatic or cycloaliphatic polyisocyanates, are based on phosgenation of the corresponding organic polyamines to form polycarbamic acid chlorides and thermal dissociation of these to give the polyisocyanates and hydrogen chloride. Apart from the serious problems in respect of environmental protection, disposal and safety associated with the use of phosgene, these processes suffer from further critical disadvantages. Thus, the preparation of aliphatic or cycloaliphatic polyisocyanates gives only quite moderate space-time yields because of the relatively high basicity of the starting polyamines. A further disadvantage is the formation of undesirable by-products which, even when present in traces, can lead to severe discoloration of the polyisocyanates. In the case of the preparation of hexamethylene 1,6-diisocyanate (HDI), for example, a number of by-products and the most important of these, viz. 6-chlorohexyl isocyanate, has the additional disadvantage that it can be separated off from HDI only with a considerable outlay for distillation.

This type of process suffers from the problems of, in particular, the high conversion of chlorine via phosgene and carbamoyl chloride into hydrogen chloride, the toxicity of phosgene and the corrosive nature of the reaction mixture, the lability of the solvents which are generally used and the formation of halogen-comprising residues.

Although the thermal dissociation of (cyclo)aliphatic and in particular aromatic monomeric urethanes and diurethanes into the corresponding isocyanates and alcohol has been known for a long time and can be carried out both in the gas phase at elevated temperatures and in the liquid phase at comparatively low temperatures, the undesirable secondary reactions and especially the tendency of the reaction mixtures to form deposits, resinous materials and blockages in reactors and work-up apparatuses, in particular, continue to impair the economics of the processes.

In past decades, many efforts have been made to eliminate these disadvantages of the process by means of a simpler and improved process. Thus, primary aliphatic and/or cycloaliphatic diamines and/or polyamines have been reacted with O-alkylcarbamic esters in the presence of alcohols at temperatures of from 160 to 300° C. with and without catalyst to prepare aliphatic and/or cycloaliphatic diurethanes and/or polyurethanes, as described in EP 18588 A1 or in EP 28338 A2. The diurethanes and/or polyurethanes formed can be converted into the corresponding isocyanates. The ammonia formed in the reaction of the amines can be separated off.

Further publications are concerned with the partial substitution of urea and/or diamines by compounds comprising carbonyl groups (e.g. EP 27952 or EP 126299). The phosgene-free process is comprehensively described in, for example, EP 566925 A2.

A disadvantage of the latter process is the relatively long reaction time, which is indicated to be up to 50 hours.

WO 2007/31444 discloses a process for preparing isocyanates by dissociation of the corresponding urethanes, in which the corresponding amine is mixed with urea and at least one alcohol together in a mixing apparatus and reacted with one another.

A conversion of up to 10% takes place in the mixing apparatus and the remaining conversion occurs in an attached reactor system.

Although this way of carrying out the reaction has already been greatly optimized, a further reduction in the by-products formed in the reaction is desirable.

It is an object of the present invention to prepare distillable organic polyisocyanates, in particular aliphatic and cycloaliphatic diisocyanates, inexpensively and in a simple manner with high selectivity in improved space-time yields without the use of costly and/or hazardous starting materials or auxiliaries. In particular, a smaller amount of by-products than in the processes of the prior art should be formed.

This object is achieved by a process for preparing isocyanates by reaction of at least one amine with urea and at least one alcohol to form the corresponding urethane in at least one mixing apparatus having at least one attached residence reactor and subsequent dissociation of the resulting urethanes into the corresponding isocyanates, in which at least part of the amine and at least part of the at least one alcohol as a mixture are mixed with urea and any remaining amine and any remaining alcohol in the at least one mixing apparatus and allowed to react.

The invention also provides a multistage process for the continuous preparation of organic isocyanates by reaction of the corresponding organic amines with urea and at least one alcohol to form the corresponding urethanes in at least two mixing apparatuses with downstream reactor and thermal dissociation thereof, which comprises the following steps and in which 0) at least part of at least one, preferably precisely one, organic amine and at least part of at least one, preferably precisely one, alcohol are mixed, optionally in the presence or preferably in the absence of at least one catalyst, in at least one first mixing apparatus to form a premixture, a) this premixture and optionally the remaining organic amine and optionally the remaining further alcohol are allowed to react partially with urea in the presence or preferably in the absence of at least one catalyst in at least one second mixing apparatus, b) the mixture obtained from a) is essentially completely reacted in at least one attached residence reactor or a plurality of residence reactors which have a residence time distribution resembling a tube reactor, c) the ammonia formed is separated off, d) excess alcohol and further low-boiling secondary components are separated off from the output from c), e) the urethane from (d) which has been freed of alcohol and low-boiling components is fed at least partly to a distillation, f) the urethanes in the distillate from (e) and any part of the output from (d) which has not been fed to the distillation (e) are dissociated in a continuous dissociation apparatus into the corresponding isocyanate and alcohol, g) the crude isocyanate obtained from (f) is purified in at least one distillation and distillation residues obtained are fed back to the dissociation (f) and/or converted by means of alcohol into urethanes and fed to the reaction unit (b) and h) the reaction output from (f), which comprises a high proportion of urethanes and usable compounds, is again converted into urethanes by reaction with alcohols.

The process of the invention has shorter residence times to achieve a prescribed conversion and thus a better space-time yield than in the processes known from the prior art, in particular the process known from EP 566 925. Compared to WO 2007/31444, the process of the invention produces a product mixture having a smaller proportion of by-products.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

Figure 1:
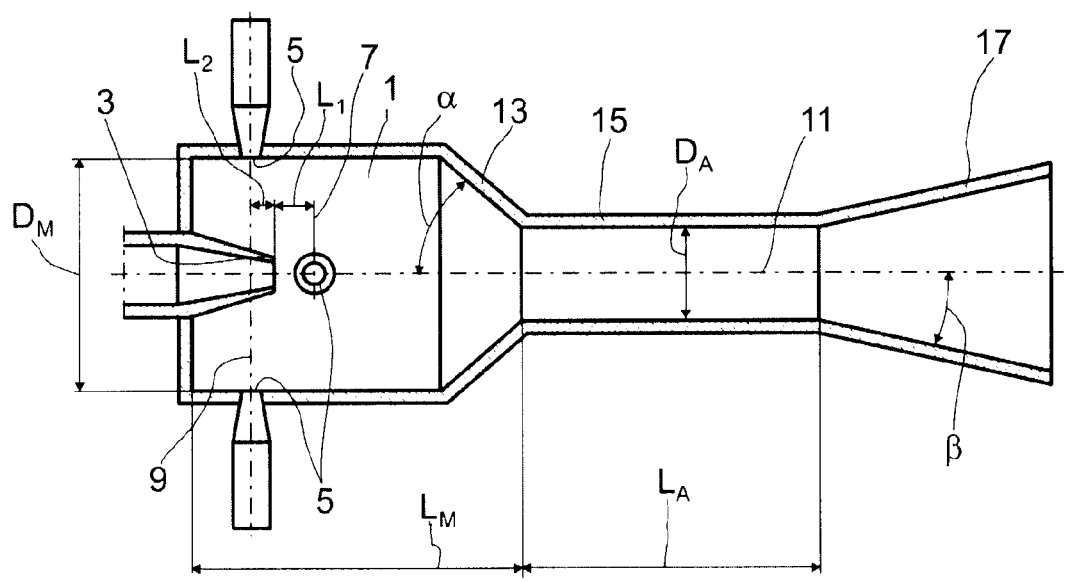
FIG. 1 shows a chamber nozzle.

Suitable amines for preparing the monomeric polyurethanes which can be used according to the invention as intermediates are amines of the formula $R(NH_2)_n$, where R is a polyvalent, preferably divalent, organic radical, e.g. an optionally substituted, for example alkyl-substituted, aromatic or preferably linear or branched, aliphatic or optionally substituted cycloaliphatic radical.

Examples of suitable aromatic polyamines are 2,4- and 2,6-toluenediamine, 4,4'-, 2,4'- and 2,2'-diaminodiphenylmethane and the corresponding isomer mixtures.

Possible aliphatic or cycloaliphatic polyamines are, for example: 1,4,-butanediamine, 2-ethyl-1,4-butanediamine, 1,8-octanediamine, 1,10-decanediamine, 1,12 dodecane-diamine, 1,4-cyclohexanediamine, 2-methyl- and 4-methyl-1,3-cyclohexanediamine, 1,3- and 1,4-diaminomethylcyclohexane, and 3 (or 4), 8 (or 9)-bis(aminomethyl)tricyclo [5.2.1.0$^{2.6}$]decane isomer mixtures. Preference is given to using 2-methyl-1,5-pentanediamine, 2,2,4- or 2,4,4-trimethyl-1,6-hexanediamine, and in particular 1,6-hexanediamine and 3-aminomethyl-3,5,5-trimethylcyclohexylamine.

The alcohol can, for example, have 2-18, particularly preferably 2-7, carbon atoms. The alcohol can be unbranched, branched or cyclic.

In an embodiment of the invention, the alkyl chain of the corresponding alcohol can be modified by heteroatoms. The heteroatoms can be halogen atoms, preferably fluorine atoms and/or chlorine atoms, particularly preferably fluorine atoms. In another embodiment, the heteroatoms are oxygen atoms. These are preferably present as ether groups.

Preferred alcohols are all aliphatic alcohols. However, preference is given to selecting those whose boiling points are sufficiently far from the boiling point of the polyisocyanate obtained by means of the thermal dissociation, preferably diisocyanate, so that virtually quantitative separation of the dissociation products polyisocyanate, preferably diisocyanate, and alcohol is possible.

For these reasons, preference is given to using alcohols such as methanol, ethanol, n-propanol, n-butanol, isobutanol, n-pentanol, isopentanol, n-hexanol, isohexanols, 2-ethylhexanol, decanol or mixtures of the alcohols mentioned, but in particular n-butanol and/or isobutanol.

The individual steps of the process are described below:
0) Premixing of Amine and Alcohol In step (0), at least part of the total amine used in the reaction and at least part of the total alcohol used in the reaction are mixed with one another in a first mixing apparatus.

Preference is given to introducing from 10 to 100% of the total amine used in the reaction into step (0), particularly preferably from 25 to 100%, very particularly preferably from 50 to 100%, in particular from 75 to 100% and especially 100%.

Preference is given to introducing from 10 to 100% of the total alcohol used in the reaction into step (0), particularly preferably from 25 to 100%, very particularly preferably from 50 to 100%, in particular from 75 to 100% and especially 100%.

The stoichiometry desired in step (a) is used as a basis for determining the total amine or alcohol used in the reaction (see under step a).

If a catalyst is to be used in the reaction, this can be introduced in step (0), for example together with the amine stream fed in or preferably the alcohol stream fed in, but any catalyst used is preferably introduced only in step (a).

According to the invention, it is important that at least part of the amine and at least part of the at least one alcohol are fed in the form of a mixture, for the purposes of the present text referred to as premix or premixture, into step (a).

The way in which this premix is produced is not important for the purposes of the invention.

It is important for the purposes of the invention that at least 95.5% of the fluid elements of the premixture have a mixing fraction which, based on the value of the theoretical final value of the mixing fraction of the mixture obtained on reaching the state of perfect mixing, deviates by less than 2% from this final value of the mixing fraction (for the concept of the mixing fraction, see, for example, J. Warnatz, U. Maas, R. W. Dibble: Verbrennung, Springer Verlag, Berlin Heidelberg New York, 1997, 2nd edition, p. 134.).

Preference is given to mixing at least part of the amine and at least part of the at least one alcohol with one another in liquid form in each case.

Mixing of the at least one, preferably precisely one, amine with the at least one, preferably precisely one, alcohol is carried out at temperatures ranging from ambient temperature to 300° C., preferably from 20 to 250° C. and particularly preferably 100-220° C., under a pressure of from 0.1 to 30 bar abs, preferably from ambient pressure to 15 bar abs.

The temperature in step (0) is preferably selected so that the premix does not have to be heated further on being passed to step (a) but has a temperature which is sufficient to ensure the required reaction temperature after mixing with urea in step (a).

Should part of the alcohol fed to step (0) comprise dialkyl carbonates and/or alkyl carbamates, for example because it is recirculated alcohol from step d) (see below), premixing in step (0) can be carried out in the presence of dialkyl carbonates, advantageously in an amount of from 0.01 to 30 mol %, preferably from 0.02 to 10 mol %, and/or alkyl carbamates, advantageously in an amount of from 0.1 to 5 mol %, preferably from 0.2 to 2 mol %, based on the amine. As dialkyl carbonates and/or carbamic esters, preference is given to those whose alkyl radicals correspond to the alkyl radical of the alcohol used.

If dialkyl carbonate and/or alkyl carbamate are/is to be introduced into the premixture (0), it is possible for partial reaction with the amine to take place during premixing.

As indicated above, the reaction in the premixture (0) can also occur in the presence of catalysts. These are advantageously used in amounts of at least 1 ppm by weight, preferably at least 2 ppm by weight, in particular at least 5 ppm by weight, based on the weight of the reaction mixture. In general, the amount of catalyst does not have to be subject to an upper limit, but the amount is preferably not more than 100 ppm by weight, particularly preferably not more than 50 ppm by weight and very particularly preferably not more than 20 ppm by weight.

Suitable catalysts are described in more detail under step (a).

In the process of the invention, premixing of the feed streams is carried out in any mixing apparatus which results in sufficient mixing.

As mixing apparatus, preference is given to using a mixing circuit, micromixers, a stirred vessel, cascades of stirred vessels, a mixing pump, rotor-stator systems, static mixers or a nozzle mixing apparatus, for example crossflow, chamber or coaxial mixing nozzles, Y- or T-mixers, or a vortex impinging jet mixing configuration, with preference being given to stirred vessels, which may be cascaded, static mixers and Y- or T-mixers.

The pressure at the outlet from the mixing apparatus is generally above the pressure in step (a), for example in the range from 5 to 100 bar, preferably from 10 to 80 bar, particularly preferably from 10 to 50 bar.

The output from step (0) can be brought to the temperature desired in step (a) by means of a heat exchanger before being introduced into step (a).

a) Mixing of the Reaction Components

For the reaction in reaction step (a), the premixture of amine and alcohol from step (0) is mixed and reacted with urea and any remaining amine and/or alcohol which has not been used in step (0) in a molar ratio of amine, urea and alcohol of 1:2-20:5-40 at temperatures of 50-300° C. and in particular 150-220° C. under a pressure of from 0.1 to 30 bar, preferably from 5-20 bar. Under these reaction conditions, average reaction times of fractions of seconds to minutes are obtained in the process of the invention.

The reaction in step (a) proceeds essentially from urea with amine to the corresponding urea, i.e. in the case of diamines essentially to the diureas. It is possible for the ureas or diureas obtained in this way to react further to a lesser extent to form the corresponding urethanes or diurethanes. The latter reaction takes place essentially in step b).

The reaction in reaction step (a) can be carried out in the presence of dialkyl carbonates, advantageously in an amount of from 0.01 to 30 mol %, preferably from 0.02 to 10 mol %, and/or alkyl carbamates, advantageously in an amount of from 0.1 to 5 mol %, preferably from 0.2 to 2 mol %, based on the polyamine, preferably diamine. In particular, mixtures of dialkyl carbonates and alkyl carbamates in the ratios mentioned are used. As dialkyl carbonates and/or carbamic esters, preference is given to using those whose alkyl radicals correspond to the alkyl radical of the alcohol used.

As indicated above, the reaction in reaction step (a) can also be carried out in the presence of catalysts. These are advantageously used in amounts of at least 1 ppm by weight, preferably at least 2 ppm by weight, in particular at least 5 ppm by weight, based on the weight of the reaction mixture. In general, the amount of catalyst does not have to be subject to any upper limit, but the amount is preferably not more than 100 ppm by weight, particularly preferably not more than 50 ppm by weight and very particularly preferably not more than 20 ppm by weight.

Suitable catalysts are inorganic or organic compounds, which comprise one or more cations, preferably one cation, of metals of groups IA, IB, IIA, IIB, IIIB, IVA, IVB, VA, VB, VIIB, VIIB, VIIIB of the Periodic Table of the Elements, as defined in Handbook of Chemistry and Physics 14th Edition, published by Chemical Rubber Publishing Co., 23 Superior Ave. N.E., Cleveland, Ohio. Examples which may be mentioned are the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron and cobalt.

The catalyst can further comprise at least one anion, for example halides, such as chlorides and bromides, sulfates, phosphates, nitrates, borates, alkoxides, phenoxides, sulfonates, oxides, hydrated oxides, hydroxides, carboxylates, chelates, carbonates and thiocarbamates or dithiocarbamates.

The catalysts can also be used in the form of their hydrates or ammoniates without significant disadvantages.

As typical catalysts, mention may be made by way of example of the following compounds: lithium methoxide, lithium ethoxide, lithium propoxide, lithium butoxide, sodium methoxide, potassium tert-butoxide, magnesium methoxide, calcium methoxide, tin(II) chloride, tin(IV) chloride, lead acetate, lead phosphate, antimony(III) chloride, antimony(V) chloride, aluminum acetylacetonate, aluminum isobutoxide, aluminum trichloride, bismuth(III) chloride, copper(II) acetate, copper(II) sulfate, copper(II) nitrate, bis (triphenylphosphine oxide)copper(II) chloride, copper molybdate, silver acetate, gold acetate, zinc oxide, zinc chloride, zinc acetate, zinc acetylacetonate, zinc octoate, zinc oxalate, zinc hexylate, zinc benzoate, zinc undecylenate, cerium(IV) oxide, uranyl acetate, titanium tetrabutoxide, titanium tetrachloride, titanium tetraphenoxide, titanium naphthenate, vanadium(III) chloride, vanadium acetylacetonate, chromium(III) chloride, molybdenum(VI) oxide, molybdenum acetylacetonate, tungsten(VI) oxide, manganese(II) chloride, manganese(II) acetate, manganese(III) acetate, iron (II) acetate, iron(III) acetate, iron phosphate, iron oxalate, iron(III) chloride, iron(III) bromide, cobalt acetate, cobalt chloride, cobalt sulfate, cobalt naphthenate, nickel chloride, nickel acetate and nickel naphthenate and also mixtures thereof.

As preferred catalysts, mention may be made by way of example of the following compounds: lithium butoxide, aluminum acetylacetonate, zinc acetylacetonate, titanium tetrabutoxide and zirconium tetrabutoxide.

In the process of the invention, mixing of the feed streams occurs in a suitable special mixing apparatus which has short mixing times.

The mixing time in this mixing apparatus is usually from 0.0001 s to 2 s, preferably from 0.0005 to 1 s, particularly preferably from 0.001 to 0.5 s, very particularly preferably from 0.005 to 0.2 s and in particular from 0.007 to 0.1 s. For the present purposes, the mixing time is the time which elapses from the commencement of mixing until 95.5% of the fluid elements of the mixture obtained have a mixing fraction which, based on the value of the theoretical final value of the mixing fraction of the mixture obtained on reaching the state of perfect mixing, deviates by less than 2% from this final value of the mixing fraction (for the concept of the mixing fraction, see for example, J. Warnatz, U. Maas, R. W. Dibble: Verbrennung, Springer Verlag, Berlin Heidelberg N.Y., 1997, 2nd edition, p. 134.).

As mixing apparatus, preference is given to using a mixing circuit, a stirred vessel, rotor-stator systems, a mixing pump or a nozzle mixing apparatus, for example crossflow, chamber or coaxial mixing nozzles, Y- or T-mixers or a vortex impinging jet mixing configuration, preferably a mixing circuit, a stirred vessel, a mixing pump or a nozzle mixing apparatus.

FIG. 1 shows a chamber nozzle as is preferably used in step (a).

Here, the reference numerals have the following meanings:

| | |
|---|---|
| 1 | Mixing chamber |
| 3 | Opening coaxial to the mixing chamber |
| 5 | Feed opening |
| 7 | First plane |
| 9 | Second plane |

-continued

| | |
|---|---|
| 11 | Axis |
| 13 | Diameter reduction |
| 15 | Zone of constant diameter |
| 17 | Widening of the cross section |
| $D_A$ | Diameter of the zone 15 of constant diameter |
| $D_M$ | Diameter of the mixing chamber 1 |
| $L_A$ | Length of the zone 15 of constant diameter |
| $L_M$ | Length of the mixing chamber 1 |
| $L_1$ | Distance from the first plane 7 to the opening 3 |
| $L_2$ | Distance from the second plane 9 to the opening 3 |
| α | Angle of the diameter reduction 13 |
| β | Opening angle of the widening of the cross section 17 |

An apparatus for mixing the premix with urea comprises a mixing chamber 1 into which urea and premix are fed. The premix is preferably introduced through an opening 3 which is arranged coaxially to the mixing chamber 1. As an alternative, it is also possible for the urea to be fed in through the opening 3 arranged coaxially to the mixing chamber. However, preference is given to introducing the urea via the opening 3 arranged coaxially to the mixing chamber. The opening 3 arranged coaxially to the mixing chamber 1 is, for example as shown here, configured in the form of a nozzle which projects into the mixing chamber 1.

Furthermore, the apparatus for mixing urea and premix comprises feed openings 5 through which the urea or, in the case of addition of the urea via the opening arranged coaxially to the axis of the mixing chamber, the premix is introduced. The feed openings 5 are likewise preferably configured as nozzles. The feed openings 5 are arranged in at least two planes 7, 9 which are arranged perpendicular to the axis of the mixing chamber. The planes 7, 9 are shown here as broken lines. In the embodiment shown here, the feed openings 5 are arranged in two planes 7, 9. A first plane 7 is arranged downstream of the coaxially arranged opening 3 and a second plane 9 is located upstream.

Apart from the embodiment having two planes 7, 9 in which the feed openings 5 are arranged which is shown here, it is also possible, as an alternative, for the feed openings to be arranged in more than two planes. If the feed openings 5 are arranged in more than two planes 7, 9, at least one plane is arranged upstream and at least one plane is arranged downstream of the coaxially arranged opening 3.

Preference is given to two feed openings 5 being arranged in each plane 7, 9, with the feed openings 5 in each case being diametrically opposite one another. As a result of the arrangement in which the feed openings 5 are diametrically opposite one another, the main directions of the feed openings 5 meet in the axis 11 of the mixing chamber 1.

The ratio of the distance $L_1$ between the first plane 7 and the opening 3 arranged coaxially to the mixing chamber to the diameter $D_M$ of the mixing chamber 1 is preferably in the range from 0 to 1, more preferably in the range from 0.01 to 0.5 and in particular in the range from 0.05 to 0.2. When feed openings 5 are arranged in more than one plane downstream of the opening 3 arranged coaxially to the mixing chamber, this is the distance of the plane which is closest to the opening 3 arranged coaxially to the mixing chamber.

The ratio of the distance $L_2$ between the second plane 9 which is arranged upstream of the opening 3 arranged coaxially to the mixing chamber 1 to the diameter $D_M$ of the mixing chamber 1 is likewise preferably in the range from 0 to 1, more preferably in the range from 0.01 to 0.5 and in particular in the range from 0.05 to 0.2. If feed openings 5 are arranged in more than two planes upstream of the opening 3 arranged coaxially to the mixing chamber 1, this corresponds to the distance of the plane which is closest to the opening 3.

At its downstream end, the mixing chamber 1 has a diameter reduction 13. The diameter reduction 13 is preferably conical and has an angle α in the range from 10 to 90°, preferably an angle in the range from 15 to 60° and particularly preferably an angle of from 18 to 40°, to the axis 11 of the mixing chamber 1.

The diameter reduction 13 is adjoined by a zone of constant diameter 15. The zone 15 of constant diameter has a diameter $D_A$, with the ratio of the diameter $D_A$ of the zone 15 of constant diameter to the diameter $D_M$ of the mixing chamber 1 as described above being in the range from 0.2 to 0.7, more preferably in the range from 0.25 to 0.65 and in particular in the range from 0.3 to 0.6. The diameter reduction 13 decreases the diameter from the diameter $D_M$ of the mixing chamber 1 to the diameter $D_A$ of the zone 15 of constant diameter.

The zone 15 of constant diameter is adjoined by a widening of the cross section 17. The widening of the cross section 17 is preferably configured in the form of a diffusor. The widening of the cross section 17 has an opening angle β which is selected so that no detachment of the flow occurs in the widening of the cross section 17. As an alternative to the embodiment shown here which has a conical widening of the cross section 17, it is also possible, for example, for the diameter in the widening of the cross section 17 to be increased in steps. In this case, a region having a constant diameter is located between the individual steps in which the diameter is increased. It is also possible, as another alternative, for a region in which the diameter increases conically to be located between each of the individual steps.

However, the widening of the cross section 17 is particularly preferably conical and the opening angle β of the widening of the cross section 17 is preferably <15°, more preferably <10° and particularly preferably <8°.

The length of the widening of the cross section 17 is preferably selected so that the diameter increases to the diameter of the reactor attached to the apparatus for mixing of the premix and urea, which is not shown here.

To achieve a short residence time and high mixing rates in the mixing chamber 1, the ratio of the length $L_M$ of the mixing chamber 1 to the diameter $D_M$ is preferably in the range from 1 to 2 and in particular in the range from 1 to 1.5. The ratio of the length $L_A$ of the zone 15 of constant diameter to the diameter $D_A$ of the zone of constant diameter is preferably in the range from 1 to 10, more preferably in the range from 1.5 to 9 and in particular in the range from 2 to 8.

In a further preferred embodiment of the present invention, a coaxial nozzle is used as mixing apparatus in step (a). In a preferred embodiment, this coaxial nozzle makes it possible for the stream of the one component to draw in the second, so that the pump for conveying the second component can be dispensed with.

Figure 2:
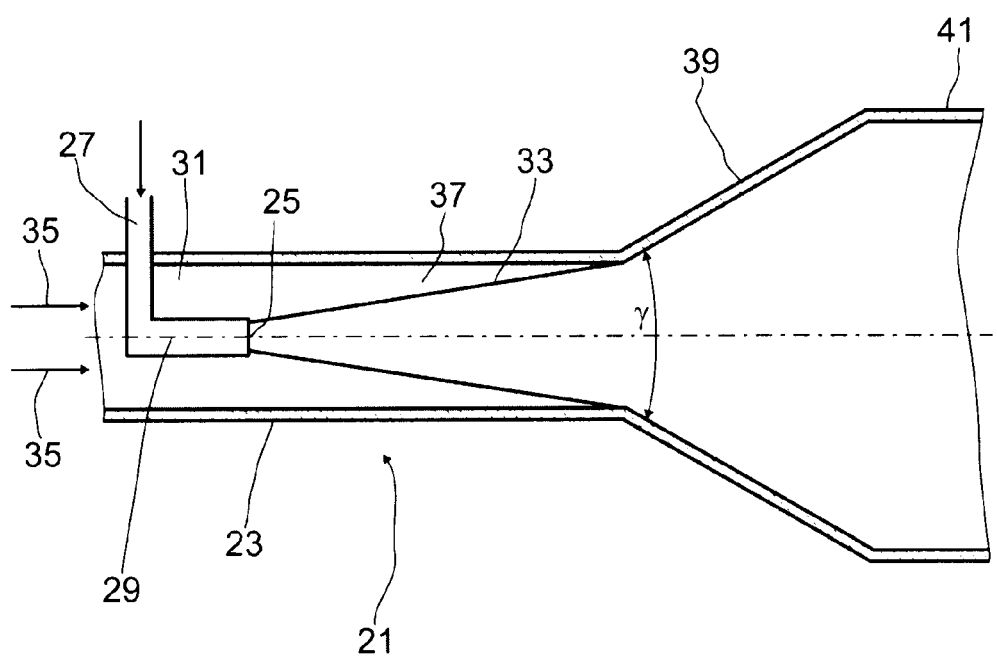
FIG. 2 shows a coaxial nozzle.
Purely formally, the process of the invention can be represented schematically by the following equation.

Such a coaxial nozzle is shown in FIG. 2.

Here, the reference numerals have the following meanings:

| | |
|---|---|
| 21 | Mixing apparatus |
| 23 | Tube |
| 25 | Central nozzle |
| 27 | Feed line |
| 29 | Section of the feed line 27 |
| 31 | Annular gap |
| 33 | Widening jet |
| 35 | Premix feed |
| 37 | Mixing zone |
| 39 | Diffusor |

| | |
|---|---|
| 41 | Reactor |
| Y | Opening angle |

A mixing apparatus 21 comprises a tube 23 into which a central nozzle 25 opens. The tube 23 encloses a feed line 27 to the central nozzle 25. The feed line 27 is tubular and has a section 29 which runs along the axis of the tube 23. In this way, an annular gap 31 is formed between the section 29 of the feed line 27 and the tube 23 surrounding the section 29 of the feed line 27.

Urea is fed via feed line 27 to the mixing apparatus 21. The urea exits from the feed line 27 via the central nozzle 25 at preferably a high velocity when the mixing apparatus is to be operated as an ejector.

The urea exiting from the central nozzle 25 forms a widening jet 33 by means of which medium from the surroundings is entrained in ejector operation. This results in a reduced pressure in the annular gap 31. As a result of the reduced pressure generated in the annular gap 31, a premix is drawn in, for example from a reservoir comprising the premix, flows through the annular gap 31 and goes into a mixing zone 37 which adjoins the central nozzle 25 in the tube 23. The inflow of the premix is indicated by arrows 35 in the figure.

The mixing apparatus can of course also be operated with premix being actively transported for example by means of a pump (stream 35). In this case, the urea 25 can be conveyed at a high velocity, but this is not absolutely necessary for operation of the mixing apparatus.

In the mixing zone 37 which adjoins the central nozzle 25 in the tube 23, the urea flowing out from the central nozzle 25 and the premix from the annular gap 31 entrained by the urea are mixed to form a mixture. Owing to the high velocity of the urea, the flow in the mixing zone 37 is turbulent and rapid mixing of premix and urea occurs.

In a preferred embodiment, the tube diameter in the mixing zone 37 is smaller than the tube diameter upstream of the point of mixing, for example at the height of the central nozzle 25. In a particularly preferred embodiment, the tube diameter decreases conically to the point of mixing.

In a further preferred embodiment, the central nozzle 25 has a smaller opening diameter than the feed tube 29.

The mixing zone 37 is adjoined by a diffusor 39. In the diffusor 39, the flow cross section generally increases constantly. For this purpose, the diffusor 39 has an opening angle $\gamma$ in the range from 4° to 20°, preferably from 6° to 16°. However, it is also possible for the opening angle $\gamma$ to increase firstly at high (from about 15 to 25°) values and subsequently steadily decreasing values (from about 4 to 10°) (bell diffusors).

In the diffusor 39, the velocity of the reaction mixture decreases and the pressure increases at the same time.

The diffusor 39 is adjoined by the reactor 41 in step (b).

Instead of the introduction of the streams described here (introduction of the urea through line 25 and of the premixture through line 35), the introduction can, as an alternative, be exchanged so that the urea is fed in through line 35 and the premixture through line 25.

When the nozzle is not operated as an ejector, the pressure in the feed lines to the nozzle is considerably higher than in the outlet of the mixing nozzle but usually not higher than 110 bar abs, preferably not higher than 100 bar abs, and the pressure is particularly preferably from 5 to 95 bar abs, very particularly preferably from 10 to 50 bar abs and in particular from 10 to 30 bar abs.

The pressure at the outlet of the mixing apparatus is generally above the reaction pressure in step b), for example in the range from 5 to 100 bar, preferably from 10 to 80 bar, particularly preferably from 10 to 50 bar.

The temperature of the output from the mixing apparatus is generally in the range from 20 to 250° C., preferably 40-220° C. and particularly preferably 100-180° C.

When a mixing circuit or a stirred vessel is used as mixing apparatus, it is important that the reactants are injected at a high velocity. The velocities are usually in the range from 10 to 100 m/s, preferably from 20 to 80 m/s.

Preference is given to using a mixing nozzle and a mixing pump as mixing apparatus. Particular preference is given to using a mixing nozzle as mixing apparatus. Here, it is important that both the urea stream and the premixture stream are introduced at high velocity into the mixing nozzle. The velocities are in the range from 10 to 100 m/s, preferably from 20 to 80 m/s.

As a result of the premixing of alcohol and amine according to the invention, the conversion in the reaction of the amine with urea to form diurea, based on amino groups in the amine used in step a), is significantly higher than in comparable processes as described in WO 2007/31444.

b) Reaction of the Mixture from a)

The liquid phase leaving the mixing apparatus is then fed into at least one, preferably precisely one, tube reactor or a cascade of a plurality of backmixed reactors which in terms of their residence time distribution resemble a tube reactor.

The reactor preferably adjoins the mixing apparatus (a) directly.

A tube reactor should preferably be largely free of backmixing. This is achieved, for example, by means of the ratio of the diameter of the tube reactor to its length or by means of internals such as perforated plates, slotted plates or static mixers. The freedom from backmixing is preferably achieved by means of the ratio of length to diameter of the tube reactor.

Suitable tube reactors are, for example, tubes whose length to diameter ratio is greater than 5, preferably greater than 6, particularly preferably greater than 10.

The Bodenstein number of the tube reactor should be greater than 5, preferably greater than 6, particularly preferably greater than 10, very particularly preferably from 10 to 600 and in particular from 10 to 100.

One aspect which makes an essential contribution to the invention is the presence of a flow regime which is ideally plug flow and in reality should come as close as possible to this. For this purpose, axial mixing, i.e. mixing along the flow direction through the reactor, should be reduced as far as possible and the flow is ideally turbulent.

This is achieved in practice by high flow velocities and low cross-sectional areas, for example in flow tubes.

The tube reactor can have any orientation in space. It is preferably constructed as a vertical tube reactor through which flow particularly preferably occurs from the bottom upward.

The tube reactor can be isothermal or preferably be temperature-controlled. Temperature control can be effected by means of wall heating or by means of internal tubes or plates. Heating is preferably carried out through the wall.

Of course, the tube reactor can also comprise a plurality of tube sections connected in series, as long as freedom from backmixing continues to be ensured. If necessary, phase separators for separating liquid and gaseous phases in which ammonia formed during the reaction can be separated off so that the equilibrium of the reaction is shifted can optionally be provided along the tube reactor, for example between such tube sections.

To increase the production capacity, it is also possible according to the invention for a plurality of tube reactors to be connected in parallel.

If appropriate, further urea and/or alcohol or preferably amine can be introduced into the tube reactor, as indicated above, at one or more places, for example at the beginning and in the middle of the tube reactor.

The average residence time in the tube reactor is generally from 10 seconds to 5 hours, preferably from 20 seconds to 20 minutes, particularly preferably from 30 seconds to 10 minutes.

To keep the gas throughput for the next stage low, the output from the tube reactor can, in a preferred embodiment, be fed to a phase separator and the liquid phase taken off from the phase separator can then be fed to the next stage.

Such a phase separator is a vessel in which phase separation of gas and liquid phases is achieved by calming of the two-phase flow exiting from the cocurrent reactor and action of gravity. As an alternative, separation of the two phases in a centrifugal field, e.g. by means of a cyclone, is also possible.

The phase separator can be isothermal or preferably heated in order to prevent precipitation of sparingly soluble by-products. Heating can, for example, be effected via the outer wall or by means of a circuit comprising an external heat exchanger. When an external heat exchanger is used, normal insulation of the heat exchanger is sufficient.

The temperature in the tube reactor and in any phase separator present is generally in the range from 50° C. to 300° C., preferably from 180° C. to 220° C.

The pressure in step b) is generally in the range from 0.1 bar abs to 30 bar abs and preferably from 5 to 20 bar abs.

The transfer of the reaction output from step b) into the next step can advantageously be effected via pressure regulating valves; the pressure in step b) should generally be at least 0.1 bar above the pressure prevailing in step c). If this is not the case, the transfer can be effected, for example, by means of a pump or barometrically.

The residence time in step b) is selected so that the conversion, based on amino groups in the amine used into urethane groups, after leaving the tube reactor is at least 95%, preferably at least 98%, particularly preferably at least 99% and very particularly preferably at least 99.5%.

The total residence time in steps a) and b) together is usually less than 5 hours, preferably less than 4 hours and particularly preferably less than 3 hours.

The reaction mixture leaving (b) can, if the amine groups have been converted completely into the urethane, be fed directly to the ammonia removal (c) or it is fed to a further reactor or reactor system in order to achieve complete conversion. Reactors which can be used are further tube reactors, cascades of mixing reactors or columns having the necessary average residence time.

If the conversion, based on amino groups in the amine used into urethane groups, after leaving the tube reactor is not yet complete and is, for example, less than 95%, the output can be subjected to an after-reaction.

For this purpose, the reaction mixture can be allowed to undergo an after-reaction in a further tube reactor or else in a backmixed reactor in order to complete the conversion, preferably until the conversion is 98% or more.

For the present purposes, a backmixed reactor system is one in which the Bodenstein number of the reactor system is less than 5, preferably less than 4.

c) Ammonia Removal

To separate off the ammonia, it is advantageous to use columns, and the ammonia is preferably separated off by distillation. This gives good separation between the alcohol and ammonia. The removal is usually carried out in a pressure range of 0.01-20 bar, preferably 0.04-15 bar. The temperatures necessary depend on the alcohol or alcohol mixture used. In the case of n-butanol, the temperature is, for example, 60-150° C., preferably from 80 to 140° C.

It has been found to be advantageous for the ammonia formed to be removed immediately from the reaction mixture so that deposits of ammonium carbamate, which is formed in small amounts from ammonia and carbon dioxide by decomposition of urea, can be avoided.

This distillation unit is of a type known per se and has the usual internals. Possible column internals are in principle all customary internals, for example, trays, ordered packing and/or random packing. Among trays, preference is given to bubble cap trays, sieve trays, valve trays, Thormann trays and/or dual-flow trays, and among random packing, preference is given to packing with rings, helices, saddle bodies, Raschig Intos or Pall rings, barrel or Intalox saddles, Top-Pak etc. or braids. Preference is given to using trays, particularly preferably bubble cap trays.

The distillation column preferably has 10-20 theoretical plates.

d) Removal of the Excess Alcohol

Alcohol, dialkyl carbonates, if these have been formed or are present in the reaction mixture, or alkyl carbamate or mixtures of at least two of these components are then separated off from the resulting ammonia-depleted reaction mixture and preferably recirculated to reaction step (0) and/or (a) and/or (b).

To separate off the components, the reaction mixture is advantageously depressurized from the pressure level of reaction step (b) to a pressure in the range from 1 to 500 mbar, preferably from 10 to 100 mbar. This gives gaseous vapors which comprise predominantly alcohol and also from 0 to 30% by weight, preferably from 1 to 10% by weight, of dialkyl carbonate and/or from 1 to 50% by weight, preferably from 1 to 20% by weight, of alkyl carbamate and a liquid output which consists essentially of the monomeric polyurethane, preferably diurethane and may comprise oligourea polyurethanes and high-boiling oligomers.

The vapors obtained ($d_L$) are separated in subsequent purification steps, advantageously by distillation, preferably by rectification, and the products of value alcohol, carbonate and alkyl carbamate isolated here are recirculated individually or as a mixture, preferably to reaction step (a) for formation of the monomeric polyurethanes.

A flash evaporator is frequently used for the removal of the alcohol or the alcohol mixture by distillation. This apparatus can be a vessel or a combination of vessel and column, preferably a column, from which the alcohol or the alcohol mixture can be taken off at the top and the urethane can be taken off at the bottom. The product from the top of the column can comprise not only the alcohol but also further materials which have boiling points lower than that of the urethane. The separation is carried out in a pressure range from 0.001 to 1 bar, preferably 0.02-0.5 bar.

e) Urethane Purification

The liquid reaction mixture (d) comprising the monomeric polyurethanes, preferably diurethanes and possibly oligourea polyurethanes and high-boiling oligomers which is generally obtained as a bottom product in reaction step (d) after the vapors have been separated off can either all be fed to the next stage or is preferably divided into two substreams in a weight ratio of 5-50:95-50, preferably 10-30:90-70.

The equal-sized or preferably smaller substream is separated off by distillation in a customary distillation unit, preferably a thin film evaporator, at a temperature of from 170 to 240° C., preferably from 180 to 230° C., under a pressure of 0.001-1 bar, preferably 0.002-0.01 bar, into a product of value which comprises the polyurethanes, preferably diurethanes and the relatively low-boiling by-products ($e_L$) and by-products ($e_H$), which cannot be distilled and are separated off from the production process and usually discarded as unusable residue. The product of value (distillate) is combined with the equal-sized or preferably larger other substream and the combined polyurethanes, preferably diurethane-comprising reaction mixture is fed to the thermal dissociation (f).

As a result of this process measure in reaction step (e) the proportion of undistillable by-products in the reaction mixture which are formed during the successive part reactions and would continually increase in concentration in the reaction circuit as a result of the recirculation of usable starting material, is limited to a content of from 3 to 30% by weight, preferably from 5 to 20% by weight and a reaction which proceeds without problems with high selectivity is thereby ensured.

As distillation apparatuses it is possible to use thin film evaporators or short path evaporators. The urethane is distilled at pressures of 0.001-1 bar, preferably in the range 0.002-0.01 bar. The distillate ($e_L$) is fed to the dissociation (f).

The high-boiling bottoms ($e_H$) are preferably discarded or can, less preferably, be partly fed to the reurethanization (h). It is also conceivable for these high-boiling bottoms to be fed to, for example, a paddle drier in order to recirculate usable dissociation products, as described in WO 2007/036479.

f) Urethane Dissociation

The reaction mixture comprising polyurethanes, preferably diurethanes, which is obtained in reaction step (e) is continuously dissociated thermally at temperatures of from 200 to 300° C., preferably from 220 to 280° C., and under a reduced pressure of 0.01-0.6 bar, preferably in the range 0.02-0.1 bar, in a suitable apparatus, preferably in the absence of solvent in the liquid phase in the presence of catalysts. The conversion of polyurethane into polyisocyanate, preferably of diurethane into diisocyanate, in the apparatus for thermal dissociation can be selected largely freely as a function of the polyurethane used and is advantageously in the range from 10 to 98% by weight, preferably from 40 to 90% by weight, of the amount of polyurethane fed in.

The undissociated part of the reaction mixture, which comprises unreacted polyurethanes, oligourea polyurethanes, high-boiling oligomers and other reusable and unusable by-products, is separated off, discharged continuously ($f_H$) from the dissociation apparatus and recirculated directly or, if appropriate, after reaction with alcohol in the reurethanization (h) to reaction step (a) and/or (b).

Catalysts used for the chemical dissociation of polyurethanes are, for example, the abovementioned inorganic and organic compounds which catalyze urethane formation.

Catalysts which have been found to be particularly useful and are therefore preferably used are dibutyltin dilaurate, iron(III) acetylacetonate, cobalt(II) acetylacetonate, zinc acetylacetonate, zirconium tetra-n-butoxide and tin(II) dioctoate.

Suitable dissociation apparatus are, for example, cylindrical dissociation reactors such as tube furnaces or preferably evaporators, for example thin film evaporators or bulk evaporators, e.g. Robert evaporators, Herbert evaporators, Caddie-type evaporators, plate crackers and preferably glow plug evaporators.

The separation of the dissociation products is effected in a column in which the isocyanate is usually taken off at the side ($f_M$) and the alcohol ($f_L$) is usually taken off at the top.

g) Isocyanate Purification

The crude isocyanate mixture is freed of recombination products, by-products and, if present, the solvent in a subsequent distillation. The by-products are preferably recirculated to the thermal dissociation. A part thereof can also be discharged.

The dissociation products formed in the thermal dissociation, which are composed predominantly of alcohol, polyisocyanate, preferably diisocyanate, and partially dissociated polyurethanes, are then advantageously separated with the aid of one or more distillation columns, preferably by rectification at temperatures of from 100 to 220° C., preferably from 120 to 170° C., and a pressure of from 1 to 200 mbar, preferably from 5 to 50 mbar, into low boilers and in particular alcohol ($g_L$) and a crude polyisocyanate mixture ($g_M$) having a polyisocyanate content of from 85 to 99% by weight, preferably from 95 to 99% by weight. The relatively high-boiling by-products ($g_H$) and in particular the undissociated and partially dissociated polyurethanes obtained in the separation by distillation are preferably fed to the dissociation apparatus (f) and/or reurethanization (h).

The index "L" here denotes low-boiling streams in the individual steps, the index "H" denotes high-boiling streams and "M" denotes middle-boiling streams.

The crude polyisocyanate mixture ($g_M$) which is preferably obtained by rectification is purified by distillation at a temperature of from 100 to 180° C. and a pressure of from 1 to 50 mbar, with the individual fractions being recirculated or isolated as pure product. As indicated above, the overhead fraction obtained in the pure distillation which is preferably employed, which preferably comprises polyisocyanate, in particular diisocyanate, is, if appropriate after reaction of the free isocyanate groups with alcohol, recirculated to reaction step (a) and/or (b), the side fraction, which comprises pure polyisocyanate, in particular diisocyanate, preferably having a purity of at least 98% by weight, in particular above 99% by weight, is conveyed away to storage and the bottom fraction, which comprises the partially dissociated polyurethanes and polyisocyanates as significant components, is preferably recirculated to the dissociation apparatus for thermal dissociation.

However, in other process variants, the bottom fraction ($g_H$) can also be recirculated to the distillation column (d) for separation of the crude polyisocyanate and alcohol or to reaction step (a) and/or (b), viz. polyurethane formation. It is also possible for the bottom fraction to be divided into 2 or 3 product streams, which are preferably recirculated to polyurethane formation (a) and/or the dissociation apparatus (f) and, if appropriate, to the distillation column (g) and/or the reurethanization (h).

h) The reaction of the reaction output ($f_H$) from f) and/or distillation residues ($g_H$) from (g) are preferably fed back to the process. Here, the isocyanate groups and/or allophanates and/or ureas or other reactive constituents are reacted with alcohol and converted to urethanes. It is possible to carry out these reactions in separate reactors such as mixing reactors or flow tubes or else in (b). The alcoholysis of the residues requires temperatures of 100-250° C., preferably 150-220° C. The average residence times here are in the range from a few minutes to hours.

For this purpose, the streams ($f_H$) and/or ($g_H$) and, if appropriate, part of the stream ($e_H$) for example, can be combined with alcohol in such amounts that the molar ratio of NCO groups or equivalents thereof, i.e. for example, urethane groups, to hydroxy groups is up to 1:100, preferably up to 1:20, particularly preferably up to 1:10.

The alcohol can, for example, be the low-boiling stream ($d_L$) from step (d) and/or the alcohol-comprising stream ($f_L$) from the urethane dissociation (f) and/or fresh alcohol.

The reaction mixture is reacted in the presence of or absence of catalysts for a period of from 1 to 150 min, preferably from 3 to 60 min at a temperature of from 20 to 200° C., preferably from 50 to 170° C., and a pressure of from 0.5 to 20 bar, preferably from 1 to 15 bar.

The reaction can be carried out in a continuous cascade of vessels or in a tube reactor.

Possible catalysts are in principle all compounds which promote the reaction of NCO groups with OH groups. Examples which may be mentioned are tin octoate, dibutyltin dilaurate, tin chloride, zinc dichloride, tin(II) dioctoate and triethylamine.

The multistage process of the invention for the continuous preparation of organic polyisocyanates with recirculation and discharge of the by-products enables distillable polyisocyanates, preferably diisocyanate, to be prepared with high selectivity in very good yields.

The process of the invention is particularly suitable for preparing aliphatic diisocyanates such as 2-methylpentane 1,5-diisocyanate, isomeric aliphatic diisocyanates having 6 carbon atoms in the alkylene radical and mixtures thereof and preferably hexamethylene 1,6-diisocyanate and cycloaliphatic diisocyanates, in particular 3-isocyanatomethyl-3,5,5-trimethylcyclohexyl isocyanate, by an economical method.

The polyisocyanates produced are highly suitable for producing plastics comprising urethane, isocyanurate, amide and/or urea groups by the polyisocyanate polyaddition process. They are also used for preparing polyisocyanate mixtures modified with urethane, biuret and/or isocyanurate groups. Such polyisocyanate mixtures of aliphatic or cycloaliphatic diisocyanates are used, in particular, for the production of light-resistant polyurethane paints and coatings.

In a preferred embodiment, the overhead fraction obtained in the purification of the crude polyisocyanate (f) by distillation is recirculated to reaction step (a), the side fraction, which consists essentially of pure polyisocyanate, is recirculated to a container for storage and the bottom fraction is recirculated to reaction step (a) or (d) or (a) and (d).

The following examples illustrate the invention but do not restrict it to these examples.

EXAMPLE

Comparative Example According to WO 2007/031444 A1

1,6-Hexamethylenediamine was placed in a vessel (A) at a temperature of 80° C. A second vessel was charged with n-butanol (B). A stream of 0.9 kg/h of amine, 8 kg/h of butanol and 1.8 kg/h of liquid urea (C) was fed by means of pumps into a reaction mixer (reaction mixer HMR from K-Engineering, reaction volume: 5 ml, 4000 min$^{-1}$). The streams were preheated by means of heat exchangers so that the temperature in the nozzle (D) was at least from 130° C. to 150° C.

The reaction mixture then flowed through a wall-heated tube reactor (E) having a length of 6 m (Bodenstein number about 40), an average residence time of a few seconds and a Reynolds number of about 10 000.

The reaction mixture from the flow tube is then allowed to reside in a mixing reactor (F) until complete conversion of the amine at an average residence time of about 4 hours. The temperature in the reactor is about 215° C. at a pressure of 11 bar. The reaction output comprises about 2.4 kg/h of hexamethylenedibutylurethane and can be dissociated into hexamethylene 1,6-diisocyanate and worked up in a known manner.

Example 1

1,6-Hexamethylenediamine was placed in a vessel at 80° C. n-Butanol at room temperature and urea at 135° C. were placed in two further vessels. The urea was introduced as solid into a pressure autoclave and melted. The butanol stream was preheated in a heat exchanger. This stream of 4.5 kg/h of n-butanol was mixed with the amine stream (0.43 kg/h of diamine) in an adjoining mixing apparatus as shown in FIG. 1. The mixing temperature established was sufficient to heat this mixed stream together with the liquid urea stream (0.59 kg/h) in a further mixing apparatus to 200° C. The further reactor configuration and the process parameters correspond to those of the comparative examples.

The yields achieved are somewhat higher than in the comparative example.

The invention claimed is:

1. A process for preparing an isocyanate, the process comprising:
    reacting an amine with urea and an alcohol to form the a urethane in at least one mixing apparatus comprising an attached residence reactor; and subsequently
    dissociating the urethane into an isocyanate,
    wherein a mixture comprising at least part of the amine and at least part of the alcohol is prepared and mixed with the urea and any remaining amine and any remaining alcohol in the at least one mixing apparatus and are allowed to react.

2. The process of claim 1, wherein at least 95.5% of fluid elements of a mixture of the at least part of the amine and the at least part of alcohol have a mixing fraction which, based on a value of a theoretical final value of a mixing fraction of a mixture obtained on reaching a state of perfect mixing, deviates by less than 2% from said theoretical final value.

3. The process of claim 1, wherein the at least one mixing apparatus is a nozzle mixing apparatus selected from the group consisting of a crossflow nozzle apparatus, a chamber nozzle apparatus, an ejector nozzle apparatus, a coaxial mixing nozzle apparatus, a Y-mixer, and a T-mixer.

4. The process of claim 1, wherein a mixing time in the at least one mixing apparatus is from 0.0001 s to 2 s.

5. The process of claim 1, wherein a urea stream and a premixture stream are introduced into the mixing apparatus at a velocity in the range from 5 to 100 m/s.

6. The process of claim 1, wherein the amine is at least one selected from the group consisting of 1,4-butanediamine, 2-ethyl-1,4-butanediamine, 1,8-octanediamine, 1,10-decanediamine, 1,12-dodecanediamine, 1,4-cyclohexanediamine, 2-methyl-1,3-cyclohexanediamine, 4-methyl-1,3-cyclohexanediamine, 1,3-diaminomethylcyclohexane, 1,4-diaminomethylcyclohexane, 2-methyl-1,5-pentanediamine, 2,2,4-trimethyl-1,6-hexanediamine, 2,4,4-trimethyl-1,6-hexanediamine, 1,6-hexanediamine, 3-aminomethyl-3,5,5-trimethylcyclohexylamine, 1,3-diaminomethylcyclohexane, 1,4-diaminomethylcyclohexane, 3-bis(aminomethyl)tricyclo [5.2.1.0$^{2.6}$] decane, 4-bis(aminomethyl)tricyclo [5.2.1.0$^{2.6}$]decane, 8-bis(aminomethyl)tricyclo[5.2.1.0$^{2.6}$] decane, 9-bis(aminomethyl)tricyclo[5.2.1.0$^{2.6}$]decane, and mixtures thereof.

7. The process of claim 1, wherein the alcohol is at least one selected from the group consisting of methanol, ethanol, n-propanol, n-butanol, isobutanol, n-pentanol, isopentanol, n-hexanol, an isohexanol, 2-ethylhexanol, decanol, and mixtures thereof.

8. The process of claim 2, wherein a mixing time in the at least one mixing apparatus is from 0.0001 s to 2 s.

9. The process of claim 3, wherein a mixing time in the at least one mixing apparatus is from 0.0001 s to 2 s.

10. The process of claim 2, wherein a urea stream and a premixture stream are introduced into the mixing apparatus at a velocity in the range from 5 to 100 m/s.

11. The process of claim 3, wherein a urea stream and a premixture stream are introduced into the mixing apparatus at a velocity in the range from 5 to 100 m/s.

12. The process of claim 2, wherein the amine is at least one selected from the group consisting of 1,4-butanediamine, 2-ethyl-1,4-butanediamine, 1,8-octanediamine, 1,10-decanediamine, 1,12-dodecanediamine, 1,4-cyclohexanediamine, 2-methyl-1,3-cyclohexanediamine, 4-methyl-1,3-cyclohexanediamine, 1,3-diaminomethylcyclohexane, 1,4-diaminomethylcyclohexane, 2-methyl-1,5-pentanediamine, 2,2,4-trimethyl-1,6-hexanediamine, 2,4,4-trimethyl-1,6-hexanediamine, 1,6-hexanediamine, 3-aminomethyl-3,5,5-trimethylcyclohexylamine, 1,3-diaminomethylcyclohexane, 1,4-diaminomethylcyclohexane, 3-bis(aminomethyl)-tricyclo[5.2.1.0$^{2.6}$]decane, 4-bis(aminomethyl)tricyclo[5.2.1.0$^{2.6}$]decane, 8-bis(aminomethyl)tricyclo[5.2.1.0$^{2.6}$]decane, 9-bis(aminomethyl)tricyclo[5.2.1.0$^{2.6}$]decane, and mixtures thereof.

13. The process of claim 3, wherein the amine is at least one selected from the group consisting of 1,4-butanediamine, 2-ethyl-1,4-butanediamine, 1,8-octanediamine, 1,10-decanediamine, 1,12-dodecanediamine, 1,4-cyclohexanediamine, 2-methyl-1,3-cyclohexanediamine, 4-methyl-1,3-cyclohexanediamine, 1,3-diaminomethylcyclohexane, 1,4-diaminomethylcyclohexane, 2-methyl-1,5-pentanediamine, 2,2,4-trimethyl-1,6-hexanediamine, 2,4,4-trimethyl-1,6-hexanediamine, 1,6-hexanediamine, 3-aminomethyl-3,5,5-trimethylcyclohexylamine, 1,3-diaminomethylcyclohexane, 1,4-diaminomethylcyclohexane, 3-bis(aminomethyl)-tricyclo[5.2.1.0$^{2.6}$]decane, 4-bis(aminomethyl)tricyclo[5.2.1.0$^{2.6}$]decane, 8-bis(aminomethyl)tricyclo[5.2.1.0$^{2.6}$]decane, 9-bis(aminomethyl)tricyclo[5.2.1.0$^{2.6}$]decane, and mixtures thereof.

14. The process of claim 2, wherein the alcohol is at least one selected from the group consisting of methanol, ethanol, n-propanol, n-butanol, isobutanol, n-pentanol, isopentanol, n-hexanol, an isohexanol, 2-ethylhexanol, decanol, and mixtures thereof.

15. The process of claim 3, wherein the alcohol is at least one selected from the group consisting of methanol, ethanol, n-propanol, n-butanol, isobutanol, n-pentanol, isopentanol, n-hexanol, an isohexanol, 2-ethylhexanol, decanol, and mixtures thereof.

16. The process according to claim 1, wherein from 75 to 100% of a total amine used in said reaction and from 75 to 100% of said alcohol used in said reaction are mixed, and the thus obtained mixture is mixed with urea and any remaining amine and any remaining alcohol in said at least one mixing apparatus.

17. The process according to claim 1, wherein a total amount of amine used in said reaction and a total amount of said alcohol used in said reaction arm mixed, and the thus obtained mixture is mixed with urea and any remaining amine and any remaining alcohol in said at least one mixing apparatus.

* * * * *